United States Patent [19]
Jain et al.

[11] Patent Number: 5,780,050
[45] Date of Patent: Jul. 14, 1998

[54] DRUG DELIVERY COMPOSITIONS FOR IMPROVED STABILITY OF STEROIDS

[75] Inventors: Uday Jain; Srinivasan Venkateshwaran; Charles D. Ebert, all of Salt Lake City, Utah

[73] Assignee: Theratech, Inc., Salt Lake City, Utah

[21] Appl. No.: 504,430

[22] Filed: Jul. 20, 1995

[51] Int. Cl.$^6$ .................................................. A61F 13/00
[52] U.S. Cl. .................................. 424/449; 424/448
[58] Field of Search .............................. 424/448, 449

[56] References Cited

U.S. PATENT DOCUMENTS

| | | | |
|---|---|---|---|
| 3,964,482 | 6/1976 | Gerstel | 128/260 |
| 4,954,343 | 9/1990 | Hosaka | 424/448 |
| 4,983,395 | 1/1991 | Chang | 424/448 |
| 5,023,084 | 6/1991 | Chien | 424/448 |
| 5,059,426 | 10/1991 | Chiang | 424/449 |
| 5,079,008 | 1/1992 | Sinnreich | 424/448 |
| 5,122,383 | 6/1992 | Heiber | 424/449 |
| 5,145,682 | 9/1992 | Chien | 424/448 |
| 5,176,916 | 1/1993 | Yamanala | 424/448 |
| 5,232,703 | 8/1993 | Blank | 424/449 |
| 5,252,334 | 10/1993 | Chiang | 424/448 |
| 5,376,377 | 12/1994 | Gale | 424/448 |

*Primary Examiner*—D. Gabrielle Phelan
*Attorney, Agent, or Firm*—Thorpe, North & Western, LLP

[57] ABSTRACT

A stabilized patch device for transdermal drug delivery of steroid drugs containing a 3-keto-4-en functional group is described, wherein the patch comprises an effective amount of the steroid drug and a carrier that is free of acid functional groups. The device can further contain additives such as a penetration enhancer or excipient, so long as such additives are also free of acid functional groups. The device can be either a matrix patch or a liquid reservoir patch. In a matrix patch, the carrier is a biocompatible polymeric adhesive with which the steroid drug is intimately admixed. The adhesive is preferably an acrylic polymer or copolymer. In a liquid reservoir patch, the carrier is a controlled-viscosity composition containing a thinner or thickener. Preferred steroid drugs include certain corticosteroids and sex hormones, such as progestins and androgens. A method of stabilizing such steroid drugs during storage in transdermal patches is also disclosed.

30 Claims, 2 Drawing Sheets

DRUG DELIVERY COMPOSITIONS FOR IMPROVED STABILITY OF STEROIDS

BACKGROUND OF THE INVENTION

This invention relates generally to drug delivery compositions for stabilizing steroid drugs having a 3-keto-4-en functional group in the A ring of the steroid. More particularly, the invention relates to stabilized patch devices for transdermal delivery of such steroid drugs and methods of stabilizing steroid drugs during storage in transdermal drug delivery devices.

Steroids having the 3-keto-4-en functional group include certain sex hormones and certain adrenocortical hormones (corticosteroids). The corticosteroids have numerous and diversified physiological functions and pharmacological effects. They influence carbohydrate, protein, fat, and purine metabolism; electrolyte and water balance; and the functions of the cardiovascular system, the kidney, skeletal muscle, nervous system, and other organs and tissues. Therapeutically, the corticosteroids are used for treating hormonal insufficiencies, inflammation, and other conditions, whereas the sex hormones are widely used for contraception and hormonal insufficiencies, as well as for treating other conditions.

Progesterone is secreted by the ovary, mainly from the corpus luteum, during the second half of the menstrual cycle. Abrupt decline in the release of progesterone from the corpus luteum at the end of the cycle is the main determinant of the onset of menstruation. The sequence of changes in the endometrium, brought about by progesterone during the luteal phase of the cycle and leading to the secretory endometrium, is well known. The endocervical glands are also influenced by progesterone. Further, the estrogen-induced maturation of the human vaginal epithelium is modified toward the condition of pregnancy by the action of progesterone, and the phenomenon of a rise in body temperature that correlates with the event of ovulation is caused by progesterone. During pregnancy, the developing placenta begins to secrete progesterone, and large amounts of progesterone are secreted up to the time of delivery. Also during pregnancy, and to a minor degree during the luteal phase of the cycle, progesterone, acting with estrogen, brings about a proliferation of the acini of the mammary gland. Toward the end of pregnancy, the acini fill with secretion and the vasculature of the gland is notably increased; however, only after the influences of estrogen and progesterone are withdrawn by parturition does lactation begin.

Progestins are used therapeutically for postmenopausal hormone replacement therapy to counteract the proliferative effects of estrogen on the endometrium, and for functional uterine bleeding, dysmenorrhea, premenstrual tension, endometriosis, and threatened and habitual abortion. Progestins are used diagnostically for evaluation of ovarian function. They are also used in oral contraceptives. Progestins are formulated for administration by oral dosage forms and by injection, but transdermal delivery by liquid reservoir and matrix patches is also known in the art. The stability of these drugs upon storage, however, is a significant problem, as will be explained more thoroughly below.

Testosterone is normally synthesized under the control of the testis, ovary, and adrenal cortex. The normal function of testosterone is familiar to everyone in the remarkable changes of puberty that transform a boy into a man. It is also thought that androgens are responsible for the aggressive and sexual behavior of males. Alterations in plasma levels of testosterone have been observed in women during the menstrual cycle. The androgens secreted by the ovary and adrenal cortex probably have physiological significance in women. Clinically, testosterone is used primarily to treat hypogonadism in males and to promote anabolism in both sexes.

The delivery of drugs through the derma, i.e. skin and mucosa, provides many advantages over other routes of administration. Primarily, transdermal drug delivery is a comfortable, convenient, and noninvasive way of administering drugs. The variable rates of absorption and metabolism associated with oral treatment are avoided, as are other inherent inconveniences such as gastrointestinal irritation and the like. Transdermal drug delivery also makes possible a high degree of control over blood concentrations of any particular drug. These advantages enhance patient compliance and improve the safety and efficacy of medications.

Skin is a structurally complex, relatively thick membrane. Molecules moving from the environment into and through the intact skin must first penetrate the stratum corneum and any material on its surface. Such molecules must then penetrate the viable epidermis, the papillary dermis, and the capillary walls into the bloodstream or lymph channels. To be so absorbed, molecules must overcome a different resistance to penetration in each type of tissue. Transport across the skin membrane is thus a complex phenomenon. However, it is the stratum corneum that presents the primary barrier to absorption of topical compositions or transdermally administered drugs. Recently there has been much interest in the use of mucosal membranes as sites of drug administration because of greater permeability than skin due to lack of a stratum corneum to impede penetration.

Devices for transdermal administration of drugs generally fall into either the category of liquid reservoir patches or of matrix patches. In liquid reservoir patches, the drug is stored as a liquid in a reservoir from which it diffuses to the skin. The patch includes a boundary layer that may include a rate-controlling membrane to control the release rate of the drug. In matrix patches, the drug is stored in an polymeric matrix that can be made of one or more layers for storing the drug, controlling the rate of release, and adhering to the skin. Liquid reservoir patches are easier to develop than matrix patches because of fewer problems such as incompatibility of drug and polymeric materials. Matrix patches, however, are easier to manufacture than liquid reservoir patches and are more comfortable and convenient to wear.

Liquid reservoir patches for delivery of sex hormones are known in the art. For example, Gerstel et al., U.S. Pat. No. 3,964,482, disclose a drug delivery device for percutaneously administering a drug comprising a plurality of projections and a drug reservoir containing a drug, wherein the projections extend from the reservoir and are adapted for penetrating the stratum corneum for percutaneously administering a drug from the reservoir. Matrix patches for administration of steroids are also known in the art. For example, Chiang et al., U.S. Pat. No. 5,252,334, disclose transdermal delivery of a steroid, preferably estradiol, using an adhesive matrix patch containing an acrylate adhesive, the steroid, and optionally a permeation enhancer and water-soluble polymers. Blank, U.S. Pat. No. 5,232,703, discloses an uncrosslinked, water-insoluble vinylpyrrolidone copolymer matrix for delivery of estradiol through the skin. Sinnreich et al., U.S. Pat. No. 5,079,008, disclose a polyisobutylene matrix for delivery of a drug in combination with eucalyptol and N-methyl-2-pyrrolidone penetration promoters. Chien, U.S. Pat. No. 5,023,084, discloses a transdermal progestin/estrogen matrix patch for fertility control, wherein the progestin and estrogen are dispersed in a polymeric adhesive. What has not been recognized in the art is that steroids containing the 3-keto-4-en functional group, including many of the sex hormones and corticosteroids, are unstable in the presence of acid functional groups contained in adhesives, penetration enhancers, excipients, and other components of patches, and that this instability significantly reduces the amount of such steroids upon storage in dosage forms containing such acid functional groups.

In view of the foregoing, it will be appreciated that providing steroid-containing drug compositions, especially steroid-containing matrix and liquid reservoir patches, wherein the problem of stability of the drug upon storage is greatly diminished, would be a significant advancement in the art.

OBJECTS AND SUMMARY OF THE INVENTION

It is an object of the present invention to provide a steroid-containing drug composition in which steroids containing a 3-keto-4-en functional group are stable upon storage.

It is also an object of the invention to provide a dosage form for transdermal delivery in which steroids containing a 3-keto-4-en functional group are stable upon storage.

It is another object of the invention to provide methods of making and using transdermal matrix and liquid reservoir dosage forms for delivery of steroids containing a 3-keto-4-en functional group, wherein such steroids are stable upon storage of the dosage forms.

These and other objects can be achieved by providing a stabilized patch device for transdermal delivery of a steroid drug containing a 3-keto-4-en functional group, wherein the steroid drug is stable upon extended storage of the device, comprising an effective amount of the steroid drug and a carrier, wherein the carrier is free of acid functional groups and forms no acid functional groups upon storage. Preferably, the steroid drug is selected from the group consisting of sex hormones, corticosteroids, and mixtures thereof. The steroid drug containing the 3-keto-4-en functional group can also be mixed with a steroid lacking such functional group, such as certain estrogens (such as estradiol), progestins, androgens, and corticosteroids. The stabilized patch device can be either a matrix patch or a liquid reservoir patch. In a matrix patch, the carrier comprises a biocompatible polymeric adhesive with which the steroid drug is intimately admixed, such as being dissolved or suspended in the adhesive. A preferred polymeric adhesive is a member selected from the group consisting of acrylic polymers and copolymers. In a liquid reservoir patch, the carrier comprises a controlled-viscosity composition with which the steroid drug is intimately admixed. The controlled-viscosity composition can contain a thinner or a thickener. The carrier can further comprise additives such as a penetration enhancer or excipient, so long as such additives are also free of acid functional groups.

A method of stabilizing a steroid drug containing a 3-keto-4-en functional group during storage of a transdermal drug delivery patch device containing such steroid drug comprises the step of first intimately admixing an effective amount of the steroid drug with an effective amount of a carrier, wherein the carrier has no acid functional groups and forms no acid functional groups upon storage, and then incorporating the admixed steroid drug and carrier into the transdermal drug delivery patch device as the source of the steroid drug.

DETAILED DESCRIPTION OF THE INVENTION

Figure 1:
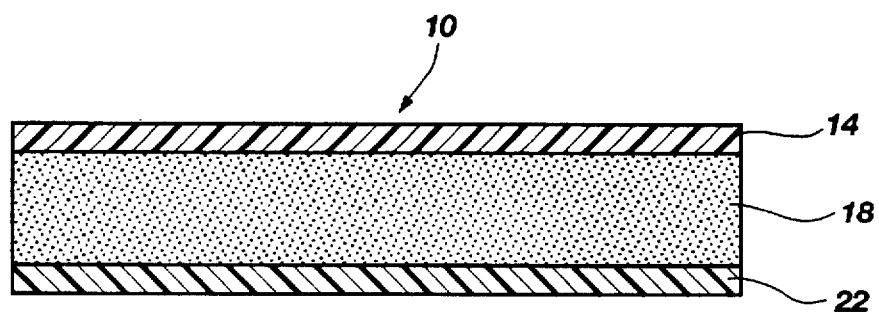
FIG. 1 shows a partly schematic, sectional view of an illustrative example of a matrix patch device according to the present invention.

Before the present stabilized steroid-containing patch device and method of stabilizing such a steroid drug during storage of such a patch device are disclosed and described, it is to be understood that this invention is not limited to the particular process steps and materials disclosed herein as such process steps and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to an adhesive layer containing "a steroid drug" includes a mixture of two or more steroid drugs, reference to "an adhesive" includes reference to one or more of such adhesives, and reference to "a penetration enhancer" includes reference to a mixture of two or more penetration enhancers.

In describing and claiming the present invention, the following terminology will be used in accordance with the definitions set out below.

As used herein, the terms "enhancement," "penetration enhancement," and "permeation enhancement" mean an increase in the permeability of a biological membrane (i.e. skin or mucosa) to a drug, so as to increase the rate at which the drug permeates through the membrane. "Permeation enhancer," "enhancer," "penetration enhancer," or similar term means a material that achieves such permeation enhancement.

As used herein, "transdermal" or "percutaneous" delivery means delivery of a drug by passage into and through the skin or mucosal tissue. Hence the terms "transdermal" and "transmucosal" are used interchangeably unless specifically stated otherwise. Likewise the terms "skin," "derma," "epidermis," "mucosa," and the like will also be used interchangeably unless specifically stated otherwise.

As used herein, "steroid drug" means a steroid containing a 3-keto-4-en functional group in the A ring thereof. Such steroid drugs include certain sex hormones, including progestins and androgens, and certain corticosteroids. Examples of such progestins include progesterone, ethisterone (17α-ethinyltestosterone), medroxyprogesterone, hydroxyprogesterone, norethindrone (17α-ethinyl-19-nortestosterone), norethindrone acetate (17α-ethinyl-19-nortestosterone acetate), dydrogesterone (9β,10α-pregna-4, 6-diene-3,20-dione), dimethisterone (6α-methyl-17α[1-propynyl]-testosterone), chlormadinone acetate (6-chloro-6-dehydro-17α-acetoxyprogesterone), norgestrel (13β-ethyl- 17α-ethinyl-17β-hydroxygon-4-en-3one), and esters and mixtures thereof. Norethindrone acetate (NEA) is a preferred progestin having the 3-keto-4-en functional group. Examples of such androgens include testosterone, methyltestosterone, fluoxymesterone, methandrostenolone, nandrolone, norethandrolone, and esters and mixtures thereof. Testosterone and esters thereof are preferred androgens having the requisite 3-keto-4-en functional group. Examples of such corticosteroids include hydroxycortisone, cortisone, desoxycorticosterone, fludrocortisone, betamethasome, dexamethasone, prednisolone, prednisone, methylprednisolone, paramethasone, triamcinolone, flumethasone, fluocinolone, fluocinonide, fluprednisolone, halcinonide, flurandrenolide, meprednisone, medrysone, and esters and mixtures thereof.

As used herein, "carrier" means a formulated component of a transdermal patch device including, but not limited to, a biocompatible polymeric adhesive, controlled-viscosity composition, penetration enhancer, excipient, diluent, emollient, plasticizer, anti-irritant, opacifier, and the like and mixtures thereof.

As used herein, "matrix," "matrix system," or "matrix patch" means a drug intimately admixed, i.e. dissolved or suspended, in a biocompatible polymeric phase, preferably a pressure sensitive adhesive, that can also contain other ingredients or in which an enhancer is also dissolved or suspended. This definition is meant to include embodiments wherein such polymeric phase is laminated to a pressure sensitive adhesive or used with an overlay adhesive. Matrix patches are known in the art of transdermal drug delivery to routinely comprise an impermeable film backing laminated onto the distal surface of the polymeric phase and, before transdermal application, a release liner on the proximal surface of the polymeric phase. A matrix patch according to the present invention should be considered to comprise such backing and release liner or their functional equivalents, and such components should also be free of acid functional groups. U.S. Pat. No. 5,122,383 describes such backing and release liner and is hereby incorporated by reference. A matrix system, therefore, is a unit dosage form of a drug composition in a polymeric carrier, also optionally containing an enhancer and other components or additives that are formulated for maintaining the drug composition in the polymeric layer in a drug transferring relationship with the derma, i.e. the skin or mucosa.

By the term "liquid reservoir patch" is meant a drug intimately admixed in a controlled-viscosity composition and contained in an occlusive device having an impermeable back surface and an opposite surface configured appropriately with a permeable membrane and adhesive for transdermal application. A peelable release liner protects the membrane and adhesive before application. A reservoir system, therefore, is a unit dosage form of a drug composition in a controlled-viscosity composition also containing an enhancer and, optionally, other components, formulated in an occlusive device for maintaining the drug composition in a drug transferring relationship with the derma, i.e. the skin or mucosa. For application, the peelable release liner is removed and the patch is attached to the skin surface. The enhancer/drug combination diffuses from the gel or ointment across the membrane and adhesive, if present, to the skin surface where the enhancer increases the permeation of the drug through the skin. Preferably, the liquid reservoir patches will be those having a peripheral adhesive ring for attachment to the skin surface such as are disclosed and claimed in U.S. Pat. No. 4,829,224 and U.S. Pat. No. 4,983,395, the disclosures of which are hereby incorporated by reference.

By "controlled-viscosity composition" is meant a vehicle or carrier in which a steroid drug and enhancer, along with any other optional additive, such as a solvent, are contained in a single or phase-separated state wherein the viscosity is controlled by addition of thinners or thickeners to achieve a selected viscosity. A controlled-viscosity composition per se can serve as a solvent, or a solvent or co-solvent can be added thereto. Such a controlled-viscosity composition can be water- or organic- based and can contain a mixture of liquids or solvents appropriately gelled or thickened. In other words, such a controlled-viscosity composition can comprise, but is not limited to, a solution, suspension, emulsion, gel, ointment, cream, paste or any other similar state that permits the outward diffusion of the steroid drug and, optionally, enhancer and/or a solvent or other additives as selected. Suitable thickeners for use in controlling the viscosity include any suitable material such as mineral oil, petroleum jelly, and various aqueous gelling agents and hydrophilic polymers such as methyl cellulose, hydroxymethylcellulose, hydroxypropylcellulose, polyvinylpyrrolidone, polyvinyl alcohol, acrylic polymer thickener (e.g. AMSCO 6038A™; Unocal), low molecular weight polymers, and the like and mixtures thereof.

As used herein, an "effective amount" of a drug means a nontoxic but sufficient amount of a drug to provide a selected effect. An "effective amount" of a penetration enhancer means an amount that provides a selected increase in membrane permeability and, correspondingly, the selected depth of penetration, rate of administration, and amount of drug.

It has been discovered that steroid drugs, i.e. steroids containing a 3-keto-4-en functional group, are unstable and subject to degradation in the presence of acid functional groups. This phenomenon occurs in any formulation, oral, injectable, or transdermal, whenever acid functional groups are present. Thus, stabilized steroid drug formulations can be fabricated by combining such steroid drugs with components, such as other drugs, carriers, excipients, and the like that are free of acid functional groups. Formulations containing non-steroidal drugs or steroids that do not contain the 3-keto-4-en functional group in a mixture with a "steroid drug" are also considered within the scope of the invention. Such mixtures can include estradiol or other estrogens combined with a progestin having the 3-keto-4-en functional group, such as norethindrone acetate, norgestrel, or progesterone, or an androgen having the 3-keto-4-en functional group, such as testesterone and esters thereof. The present invention is drawn to transdermal delivery of such steroid drugs in stabilized formulations.

The flux of a drug across the skin or mucosa can be increased by changing either the resistance (the diffusion coefficient) or the driving force (the gradient for diffusion). Flux can be enhanced by the use of penetration enhancers. Penetration enhancers are comprised of two primary categories of components, i.e. cell-envelope disordering compounds and solvents. Binary systems containing both cell-envelope disordering compounds and solvents are known in the art, e.g. U.S. Pat. No. 4,863,970, incorporated herein by reference.

Cell-envelope disordering compounds are known in the art as being useful in topical pharmaceutical preparations. These compounds are thought to assist in skin penetration by disordering the lipid structure of the stratum corneum cell envelopes. A comprehensive list of these compounds is described in European Patent Application No. 43,738, published Jun. 13, 1982, which is incorporated herein by reference. It is believed that any cell envelope disordering compound is useful for purposes of this invention as long as it contains no acid functional groups or forms no acid functional groups upon storage or aging. Preferred cell envelope disordering compounds include isopropyl myristate, methyl laurate, oleyl alcohol, glycerol monooleate, glycerol dioleate, glycerol trioleate, glycerol monostearate, glycerol monolaurate, propylene glycol monolaurate, and sorbitan esters and mixtures thereof.

Similarly, acceptable solvents that can be used in the present invention should contain no acid functional groups. Suitable solvents include water; diols, such as propylene glycol and glycerol; mono-alcohols, such as ethanol, propanol, and higher alcohols; DMSO; dimethylformamide; N,N-dimethylacetamide; 2-pyrrolidone; N-(2-hydroxyethyl) pyrrolidone, N-methylpyrrolidone, 1-dodecylazacycloheptan-2-one and other n-substituted-alkyl-azacycloalkyl-2-ones (azones) and (azones) and the like and mixtures thereof.

Other chemical enhancers, not necessarily associated with binary systems, include DMSO or aqueous solutions of DMSO such as taught in Herschler, U.S. Pat. No. 3,551,554; Herschler, U.S. Pat. No. 3,711,602; and Herschler, U.S. Pat. No. 3,711,606, and the azones (n-substituted-alkyl-azacycloalkyl-2-ones) such as noted in Cooper, U.S. Pat. No. 4,557,943.

Some chemical enhancer systems can possess negative side effects such as toxicity and skin irritation. U.S. Pat. No. 4,855,298 discloses compositions for reducing skin irritation caused by chemical enhancer-containing compositions having skin irritation properties with an amount of glycerin sufficient to provide an anti-irritating effect. Thus, anti-irritants can advantageously be added to drug-containing compositions within the scope of the invention.

Transdermal drug delivery systems are often disadvantageously subject to a "burst effect," wherein a very high dose of drug is delivered initially when a transdermal drug delivery system is applied to the derma. This burst or very high level then drops or levels off after a period of time to reach acceptable drug levels in the blood plasma. Thus, there is a highly non-uniform drug delivery profile. Copending application Ser. No. 07/897,269 describes a solution to this problem by virtue of the discovery that glycerin, when added to a transdermal formulation, effectively reduces the initial dose of a drug while maintaining a more uniform drug penetration into the bloodstream over the intended duration of application without significantly reducing the dose administered. Thus, agents that counteract the burst effect can advantageously be added to drug/enhancer compositions within the scope of the invention.

Referring to FIG. 1, an illustrative embodiment of a matrix patch device according to the present invention is shown generally at 10. The device 10 is in the form of a laminated drug-containing polymeric layer adapted to adhere to an application situs. The individual layers of the device 10 include a substantially drug-impermeable distal backing 14, a drug laden polymer layer 18, which is adapted to adhere to the skin or mucosa, and a substantially drug-impermeable proximal release liner 22.

The distal backing layer 14, in use, defines the side of the patch that faces the environment, i.e., distal to the skin or mucosa. The functions of the backing layer 14 are to protect the patch and to provide an impenetrable layer that prevents loss of the drug to the environment. Thus, the material chosen should be substantially impermeable to the drug. Advantageously, the backing material can be opaque to protect the drug from degradation from exposure to light.

Further, the backing layer 14 should be capable of binding to and supporting the other layers of the device, yet should be pliable to accommodate the movements of a person using the device 10. Materials that can be used, with or without modification, are those selected from the group consisting of metal foils, metalized polyfoils, composite foils or films containing polytetrafluoroethylene ("TEFLON®")-type materials or equivalents thereof, polyether block amide copolymers (e.g., "PEBAX" copolymers), polyurethanes such as "PELLATHANE™" or "ESTANE™" polymers, polyvinylidene chloride (Saran®), nylon, silicone elastomers, rubber-based polyisobutylene, styrene, styrene-butadiene and styrene-isoprene copolymers, polyethylene, polypropylene, polyester, and other such materials used in the art of transdermal drug delivery. As with other components of the matrix device, the material selected for the backing should not contain acid functional groups or produce acid functional groups upon aging.

The polymer used in forming the polymer/drug composite 18 should be drug compatible and permit a useful drug flux. The material comprising the polymer layer 18 is preferably a pressure-sensitive skin contact adhesive comprised of a pharmaceutically acceptable material that lacks acid functional groups and forms no acid functional groups upon storage. It should also satisfy the general criteria for adhesives used for transdermal patches including biocompatibility, ease of application, and ease of removal. The adhesive should preferably be of materials in which the drug has moderate diffusivity. After equilibration, the drug will have diffused throughout the adhesive layer 18, which is useful for regulation of release kinetics. Thus, by careful selection of the materials used for the adhesive layer 18, the distribution of drug throughout the entire device 10 can be regulated. Other useful criteria include adequate drug solubility in the adhesive layer 18 to provide reservoir capacity. Suitable adhesives for use in the practice of the invention include natural and synthetic rubbers including polyisobutylenes, neoprenes, polybutadienes, and polyisoprenes. Other suitable materials include polysiloxanes, polyurethanes, plasticized weight polyether block amide copolymers ("PEBAX" copolymers), and certain cross-linked or uncross-linked acrylic polymers and copolymers. Cross-linked and uncross-linked acrylic polymers and copolymers are preferred polymeric adhesives because they are more flexible, less expensive, provide a wider range of adhesive formulations, and provide for better solubility of drugs than do other adhesives, such as the polyisobutylene ("PIB") adhesives. Two preferred adhesives are a block copolymer of N-vinyl pyrrolidone and 2-ethyl-hexyl acrylate (TSR, Sekisui Chemical Co., Osaka, Japan) and a hydroxy functional acrylate adhesive (GELVA 737, Monsanto Polymer Products Co., St. Louis, Mo.). Although it is preferred that the polymer is an adhesive, it is considered within the scope of the invention to use a non-adhesive polymer. In such case, the polymer layer could be laminated to an adhesive or used with an adhesive overlay. In any event, the components of the matrix device that come in contact with the drug should not contain acid functional groups or form such acid functional groups upon aging.

The proximal release liner or peelable film 22 covers the skin-facing or proximal side of the device 10 until the device 10 is used. Therefore, the proximal release liner or peelable film 22 should possess properties similar to those of the backing 14, and the same materials are preferred. Just prior to use of the device, the proximal release liner 22 is removed to expose the drug-containing polymer layer 18 for contact and adhesion to the skin or mucosal surface. Thus, the proximal release liner 22 is adapted to be removed from the device 10.

A method of stabilizing a steroid drug containing a 3-keto-4-en functional group during storage of a transdermal drug delivery patch device containing such steroid drug comprises the step of first intimately admixing an effective amount of the steroid drug with an effective amount of a carrier, wherein the carrier has no acid functional groups and forms no acid functional groups upon storage, and then incorporating the admixed steroid drug and carrier into the transdermal drug delivery patch device as the source of the steroid drug. According to this method, the patch device can be either a matrix patch or a liquid reservoir patch, and the carrier can be any suitable carrier selected as hereinbefore described. The patch devices can be fabricated according to methods well known in the art.

EXAMPLE 1

Selected amounts of glycerin, glycerol monooleate (GMO), methyl laurate (ML), and ethanol were mixed to obtain a homogenous solution. Water was then added to yield a stock solution containing ethanol/water/glycerin/GMO/ML in the proportions of 56/20/20/2/2 in percent by volume. Aliquots (100 ml) of this stock solution were transferred to bottles, and NEA was added to a final concentration of about 10 mg/ml in each bottle. These NEA-containing solutions were analyzed for drug content, and then the bottles were sealed and incubated for selected lengths of time at either room temperature (RT) or 45° C. before the solutions were again analyzed for NEA content. Samples were incubated at 45° C. to accelerate decomposition that would occur at RT given sufficient time. That is, decomposition experiments could be speeded up by incubating samples at the higher temperature. NEA content was determined by HPLC analysis. The results of this experiment are shown in Table 1.

TABLE 1

| Time (Weeks) | RT (mg NEA/ml)* | 45° C. (mg NEA/ml)* |
| --- | --- | --- |
| 0 | 10.31 ± 0.21 | — |
| 12 | 10.34 ± 0.14 | 10.13 ± 0.14 |

*Mean ± SD, n = 4

These results show that NEA is relatively stable for 12 weeks at either RT or 45° C. in a drug composition containing no acid functional groups.

EXAMPLE 2

The procedure of Example 1 was followed except that to each bottle was added 1.5% by weight of hydroxypropyl cellulose (KLUCEL HXF, Aqualon Co., Wilmington, Del.). The drug content of the resulting gel was determined by placing a known amount of gel in a jar, extracting the gel with methanol overnight with agitation, and assaying the drug content of an aliquot of the methanol extract by HPLC. The results of this experiment are shown in Table 2.

TABLE 2

| Time (weeks) | RT (mg NEA/g gel)* | 45° C. (mg NEA/g gel)* |
| --- | --- | --- |
| 0 | 10.27 ± 0.15 | — |
| 12 | 10.17 ± 0.10 | 10.17 ± 0.07 |

*Mean ± SD, n = 4

These results show that NEA is relatively stable for 12 weeks at either RT or 45° C. in a gelled drug/enhancer composition containing no acid functional groups. Such gelled compositions would be useful in liquid reservoir patch or free form transdermal delivery systems.

EXAMPLE 3

The procedure of Example 2 was followed except that to each bottle was added 1.5% by weight of polyacrylic acid cross-linked with allyl ethers (CARBOPOL 1342, BF Goodrich Co., Cleveland, Ohio). Since this cross-linked polyacrylic acid reduced the pH of the drug/enhancer formulation, enough 2N NaOH was added to adjust the pH to about pH 5.5, comparable to the pH of the drug/enhancer formulations in Examples 1 and 2. The results of this experiment are shown in Table 3.

TABLE 3

| Time (weeks) | RT (mg NEA/g gel)* | 45° C. (mg NEA/g gel)* |
| --- | --- | --- |
| 0 | 10.16 ± 0.12 | — |
| 12 | 9.92 ± 0.07 | 9.21 ± 0.05 |

*Mean ± SD, n = 4

These results show that there was about 90% loss of NEA in gels containing acid functional groups when stored at 45° C. for 12 weeks. These results contrast with those of Examples 1 and 2 wherein there was no significant drug loss when acid functional groups were not present in the formulation.

Figure 2:
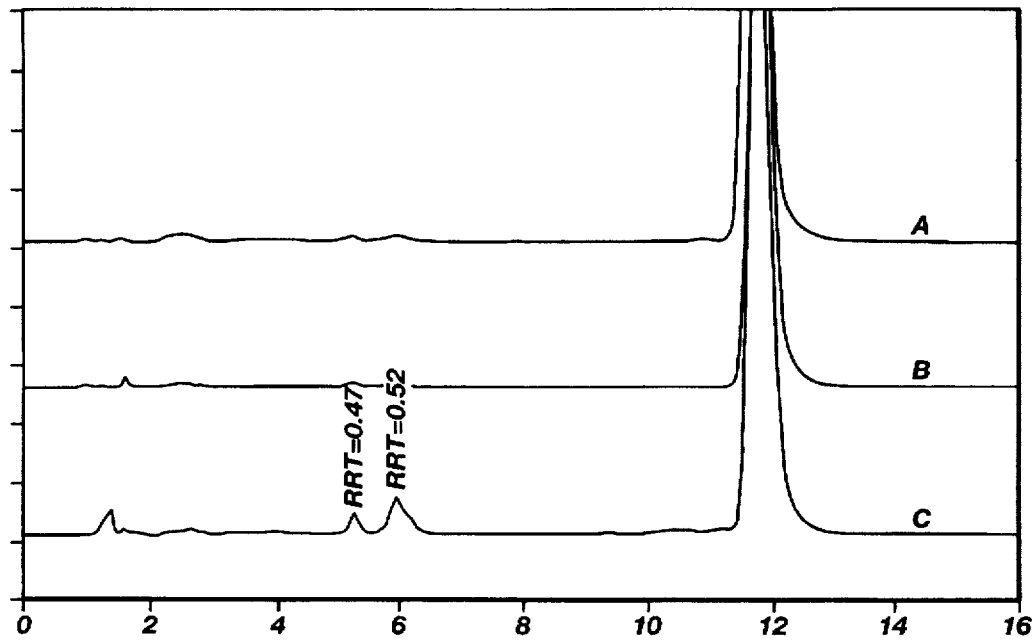
FIG. 2 shows a graphic representation of results of HPLC analysis of NEA and degradation products thereof after storage in liquid formulations containing: A-no gelling agent; B-1.5% hydroxypropyl cellulose; C-1.5% cross-linked polyacrylic acid.

HPLC analysis (FIG. 2) shows the presence of degradation products of NEA in the gels containing acid functional groups that were not present in the formulations without acid functional groups. These degradation products had relative retention times (RRT's) of 0.47 and 0.52 as compared to NEA. Samples of these degradation products were collected from the HPLC effluent, concentrated under reduced pressure, redissolved in chloroform, and analyzed by mass spectrometry. The results of this analysis showed that the degradation products were hydroxy derivatives of NEA. The positions of hydroxylation are uncertain, but are likely to be at the 6, 8, and/or 10 positions. These results demonstrate that formation of these degradation products is associated with the presence of acid functional moieties. The degradation of NEA in the presence of acid functional moieties is not a simple ester hydrolysis to norethindrone, but a nucleophilic substitution on the backbone of the NEA molecule.

EXAMPLE 4

A matrix transdermal patch containing NEA was fabricated as follows. A small amount of DuroTak 80-1196 adhesive solution (an acrylic adhesive containing acid functional groups, National Starch & Chemical Co., Bridgewater, N.J.) was dispensed into a preweighed aluminum dish, and the weight thereof was determined. The solvent was evaporated by drying overnight in a convection oven at 70° C., then the dish and its contents were weighed again. The percent solids was calculated by dividing the dry weight by the wet weight and multiplying by 100. Known amounts of DuroTak 80-1196 adhesive solution were weighed into glass bottles. From the weights of adhesive solution and the percent solid adhesive, the amount of adhesive in the solution was calculated. Appropriate quantities of NEA (Schering AG, Berlin, Germany) and sorbitan monooleate penetration enhancer (ARLACEL 80, ICI Americas, Wilmington, Del.) were added to yield compositions containing 81% DuroTak 80-1196, 4% NEA, and 15% sorbitan monooleate, all percentages being calculated on a dry weight basis. Each glass bottle was then tightly capped, sealed with laboratory film (PARAFILM "M", American National Can Co., Greenwich, Conn.), and gently agitated overnight until all ingredients had completely dissolved and the solution was clear.

About 8 ml of the DuroTak 80-1196/NEA/sorbitan monooleate solution was then dispensed on a siliconized polyester release liner (Release Technologies, Inc., W. Chicago, Ill.) and cast with a 10 mil gap casting knife. This cast mixture was dried in a convection oven at 70° C. for 15 minutes to yield a dry film about 2 mil thick. A polyethylene backing film (3M Corp., St. Paul, Minn.) was then laminated onto the dry adhesive film using a rubber roller. This matrix laminate was used for accelerated drug stability evaluations.

The stability of NEA in matrix patches formulated according to this example was determined as follows. Patches (10 cm$^2$) were hand cut from the matrix laminate, placed in white 3×3 inch pouches (laminates of SURLYN, aluminum foil, low density polyethylene, and paper; WRAPS, Inc., East Orange, N.J.), heat sealed in the pouches, and stored at room temperature (RT) or at 45° C. Sample patches were analyzed for drug content at time zero and at selected intervals thereafter. Three samples stored at each temperature were weighed before and after peeling the release liner from the patches. The average weight of the backing film was determined by weighing 10 backing film samples of the same dimensions as the patches. The weight of adhesive in each patch was calculated by subtracting the weight of the backing film from the weight of the patch with the release liner removed. The peeled patches were then extracted for 24 hours in a tightly sealed container with 50 ml of methanol. The methanol extracts were analyzed by HPLC to determine the drug content of each patch. The results of this accelerated stability study are shown in Table 4.

TABLE 4

| Time (weeks) | RT (% w/w)* | 45° C. (% w/w)* |
|---|---|---|
| 0 | 3.88 ± 0.03 | — |
| 14 | 3.80 ± 0.02 | 2.5 ± 0.00 |

*Mean ± SD (n = 3)

Figure 3:
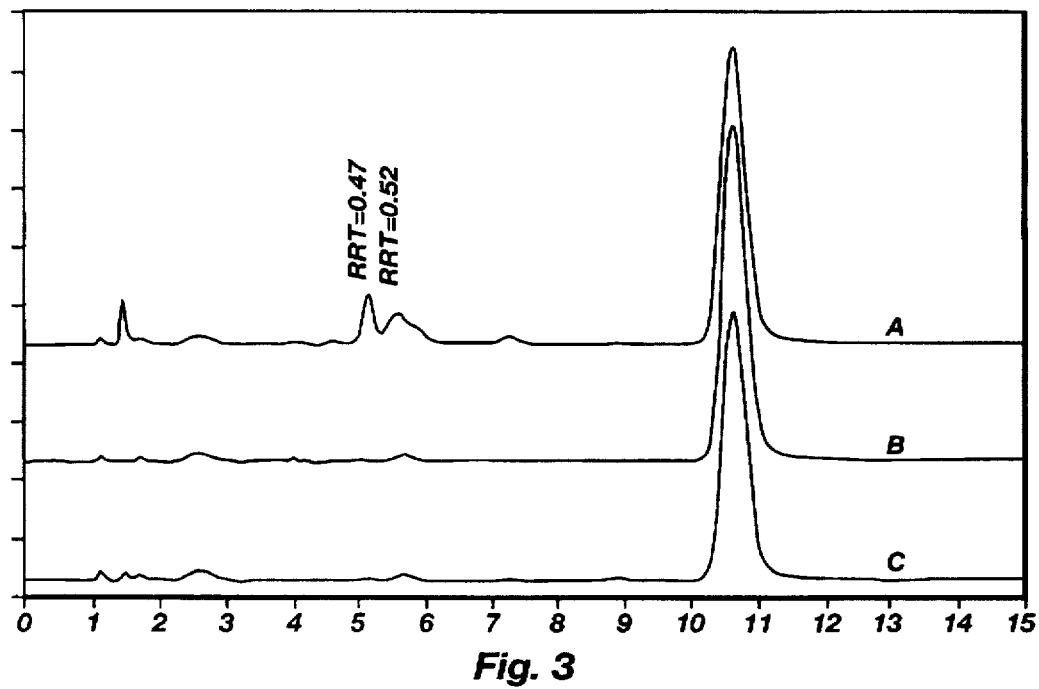
FIG. 3 shows a graphic representation of results of HPLC analysis of NEA and degradation products thereof after storage in at room temperature for 114 weeks in matrix formulations containing: A-81% (w/w) DuroTak 80-1196, 4% (w/w) NEA, 15% (w/w) sorbitan monooleate; B-81% (w/w) TSR, 4% (w/w) NEA, 15% (w/w) sorbitan monooleate; C-81% (w/w) GELVA 737, 4% (w/w) NEA, 15% (w/w) sorbitan monooleate.

These results indicate that about 36% of NEA was lost due to decomposition after 14 weeks of storage at 45° C. in the presence of an adhesive containing acid functional groups. FIG. 3 shows that this loss of drug content upon storage in the presence of acid functional groups is associated with formation of degradation products with RRT's identical to those of Example 3 (FIG. 2), suggesting that the degradation of NEA is by the same mechanism as in Example 3.

EXAMPLE 5

A matrix transdermal patch containing NEA was fabricated according to the procedure of Example 4 with the exception that the adhesive was an acrylic copolymer (copolymer of 2-ethylhexyl acrylate and n-vinyl-2-pyrrolidone; TSR, Sekisui Chemical Co., Osaka, Japan) containing no free acid functional groups. A formulation containing the following percentages of ingredients on a dry weight basis was prepared: 81% TSR, 4% NEA, 15% sorbitan monooleate. The stability of NEA in these patches was determined according to the procedure of Example 4, the results of which are shown in Table 5.

TABLE 5

| Time (weeks) | RT (% w/w)* | 45° C. (% w/w)* |
|---|---|---|
| 0 | 4.14 ± 0.04 | — |
| 8.5 | 4.08 ± 0.06 | 3.91 ± 0.07 |

*Mean ± SD (n = 3)

These results indicate that the NEA content of matrix patches containing no acid functional groups was relatively stable upon storage at room temperature or 45° C. for up to 8.5 weeks. NEA was further found to be stable upon storage at room temperature for more than 2 years when no acid functional groups are present. Degradation of NEA by hydroxylation was suppressed or inhibited as compared to patches containing acid functionalities (FIG. 3).

EXAMPLE 6

Matrix transdermal patches containing NEA were fabricated according to the procedure of Example 4 with the exception that the adhesive was an acrylic copolymer free of acid functional groups (GELVA 737, Monsanto Polymer Products Co., St. Louis, Mo.). A formulation containing the following percentages of ingredients on a dry weight basis was prepared: 81% GELVA 737, 4% NEA, 15% sorbitan monooleate. The stability of NEA in patches thus prepared was determined, the results of which are summarized in Table 6.

TABLE 6

| Time (weeks) | RT (% w/w)* | 45° C. (% w/w)* |
|---|---|---|
| 0 | 3.99 ± 0.06 | — |
| 8.5 | 3.87 ± 0.10 | 3.82 ± 0.12 |

*Mean ± SD

These results show that there was no significant loss of NEA upon storage for more than 8 weeks at either room temperature or 45° C. in the absence of acid functional groups. The drug has further been shown to be stable for over 2 years at room temperature in this formulation. Moreover, the formation of degradation products of NEA was suppressed or inhibited as compared to formulations containing acid functional groups (FIG. 3).

EXAMPLE 7

Matrix transdermal patches containing testosterone (TS) were fabricated according to the procedure of Example 4. A formulation containing the following percentages of ingredients on a dry weight basis was prepared: 83% DuroTak 80-1196, 2% TS, 15% sorbitan monooleate. The stability of TS in patches thus prepared was determined, the results of which are summarized in Table 7.

TABLE 7

| Time (weeks) | RT (% w/w)* | 45° C. (% w/w)* |
|---|---|---|
| 0 | 1.94 ± 0.03 | — |
| 4 | 2.05 ± 0.03 | 1.88 ± 0.03 |
| 12 | 2.05 ± 0.01 | 1.75 ± 0.03 |
| 26 | 1.98 ± 0.04 | 1.52 ± 0.05 |

*Mean ± SD

These results show that at each time point there was a significant difference in TS content between patches stored at RT and patches stored at 45° C. TS was unstable in the adhesive, which contains acid-functional groups, resulting in 12% and 24% drug loss in the 45° C. samples as compared to the RT samples. Loss of TS content in DuroTak 80-1196 adhesive was shown to be due to formation of degradation products of TS, and formation of at least one hydroxy derivative of TS was confirmed by comparison of the chromatography profiles of the degradation products and authentic 6β-OH testosterone. This example demonstrates that the steroid drug testosterone undergoes degradation in an adhesive containing acid functional groups by a nucleophilic substitution mechanism similar to that observed with NEA.

EXAMPLE 8

A matrix transdermal patch containing TS was fabricated as in Example 7 with the exception that DuroTak 80-1196 was replaced by DuroTak 87-2287 (an acrylic adhesive free of acid functional groups). A formulation containing the following percentages of ingredients on a dry weight basis was prepared: 88% DuroTak 87-2287, 2% TS, 10% sorbitan monooleate. The stability of TS in these patches was determined, the results of which are shown in Table 8.

TABLE 8

| Time (weeks) | RT (% w/w)* | 45° C. (% w/w)* |
|---|---|---|
| 0 | 2.03 ± 0.02 | — |
| 4 | 1.97 ± 0.01 | 2.01 ± 0.02 |
| 12 | 2.00 ± 0.01 | 2.02 ± 0.01 |
| 26 | 1.97 ± 0.02 | 1.91 ± 0.02 |

*Mean ± SD

These data show that there was no significant difference in TS content between the patches stored at RT and those stored at 45° C. up to 26 weeks, and the drug was stable in DuroTak 87-2287 adhesive, which is free of acid functional groups, up to 26 weeks at 45° C. These results show that steroid drug, testosterone, is stable upon storage in formulations free of acid functional groups.

EXAMPLE 9

Matrix transdermal patches containing norethindrone (NE) were fabricated according to the procedure of Example 4. A formulation containing the following percentages of ingredients on a dry weight basis was prepared: 88% DuroTak 80-1196, 2% NE, 10% sorbitan monooleate. The stability of NE in patches thus prepared was determined, the results of which are summarized in Table 9.

TABLE 9

| Time (weeks) | RT (% w/w)* | 45° C. (% w/w)* |
|---|---|---|
| 0 | 1.95 ± 0.06 | — |
| 11 | 1.97 ± 0.04 | 1.77 ± 0.05 |

*Mean ± SD

These results show that there was a significant difference in steroid drug content, about 11%, between the patches stored at RT and those stored at 45° C. The steroid drug norethindrone was thus unstable in adhesive containing acid functional groups.

EXAMPLE 10

Matrix transdermal patches containing NE were fabricated according to the procedure of Example 9 with the exception that TSR adhesive, which is free of acid functional groups, was substituted for DuroTak 80-1196. A formulation containing the following percentages of ingredients on a dry weight basis was prepared: 88% TSR, 2% NE, 10% sorbitan monooleate. The stability of NE in patches thus formulated was determined, the results of which are shown in Table 10.

TABLE 10

| Time (weeks) | RT (% w/w)* | 45° C. (% w/w)* |
|---|---|---|
| 0 | 1.96 ± 0.07 | — |
| 11 | 1.99 ± 0.08 | 1.96 ± 0.03 |

*Mean ± SD

Comparison of the data at each time point shows that there was no significant difference in steroid drug content between patches stored at RT and those stored at 45° C. up to 11 weeks, and the steroid drug was stable in adhesive free of acid functional groups up to 11 weeks at 45° C.

EXAMPLE 11

Matrix transdermal patches containing NE were fabricated according to the procedure of Example 9 with the exception that sorbitan monooleate was omitted. A formulation containing the following percentages of ingredients on a dry weight basis was prepared: 98% DuroTak 80-1196, 2% NE. The stability of NE in patches thus formulated was determined, the results of which are shown in Table 11.

TABLE 11

| Time (weeks) | RT (% w/w)* | 45° C. (% w/w)* |
|---|---|---|
| 0 | 1.97 ± 0.02 | — |
| 11 | 2.01 ± 0.02 | 1.64 ± 0.03 |

*Mean ± SD

These results show about 14% loss in NE content between patches stored at RT and those stored at 45° C. by 11 weeks. Thus, the steroid drug is unstable in a formulation containing acid functional groups. The magnitude of steroid drug loss is approximately equal to that of patches containing sorbitan monooleate (Example 9). Therefore, instability of the steroid drug is due to interaction with the acid-functional-group-containing adhesive and not the sorbitan monooleate permeation enhancer.

EXAMPLE 12

Matrix transdermal patches containing levonorgestrel (LVNG) were fabricated according to the procedure of Example 4. A formulation containing the following percentages of ingredients on a dry weight basis was prepared: 89% DuroTak 80-1196, 1% LVNG, 10% sorbitan monooleate. The stability of LVNG in patches thus prepared was determined, the results of which are summarized in Table 12.

TABLE 12

| Time (weeks) | RT (% w/w)* | 45° C. (% w/w)* |
|---|---|---|
| 0 | 1.94 ± 0.02 | — |
| 11 | 0.98 ± 0.01 | 0.84 ± 0.02 |

*Mean ± SD

These data show a significant LVNG loss, about 14%, between the patches stored at RT and those stored at 45° C. up to 11 weeks. LVNG was thus unstable in an acid-functional-group-containing adhesive.

EXAMPLE 13

Matrix transdermal patches containing levonorgestrel (LVNG) were fabricated according to the procedure of Example 12 with the exception that TSR adhesive, which contains no acid functional groups, was substituted for DuroTak 80-1196. A formulation containing the following percentages of ingredients on a dry weight basis was prepared: 89% TSR, 1% LVNG, 10% sorbitan monooleate. The stability of LVNG in patches thus prepared was determined, the results of which are summarized in Table 13.

TABLE 13

| Time (weeks) | RT (% w/w)* | 45° C. (% w/w)* |
| --- | --- | --- |
| 0 | 0.91 ± 0.03 | — |
| 11 | 0.89 ± 0.02 | 0.89 ± 0.03 |

*Mean ± SD

Comparison of these data at each time point shows no significant difference in LVNG content between patches stored at RT and those stored at 45° C. up to 11 weeks. Thus, the steroid drug was stable in an adhesive free of acid functional groups for up to 11 weeks at 45° C.

EXAMPLE 14

Matrix transdermal patches containing LVNG were fabricated according to the procedure of Example 12 with the exception that sorbitan monooleate was omitted. A formulation containing the following percentages of ingredients on a dry weight basis was prepared: 99% DuroTak 80-1196, 1% LVNG. The stability of LVNG in patches thus formulated was determined, the results of which are shown in Table 14.

TABLE 14

| Time (weeks) | RT (% w/w)* | 45° C. (% w/w)* |
| --- | --- | --- |
| 0 | 0.98 ± 0.03 | — |
| 11 | 0.99 ± 0.02 | 0.85 ± 0.03 |

*Mean ± SD

These data show a significant loss in LVNG content, about 14%, between patches stored at RT and those stored at 45° C. up to 11 weeks. This confirms that the steroid drug is unstable in the presence of acid functional groups. Comparison with Example 12 shows that the instability is due to interaction with the adhesive and is independent of sorbitan monooleate in the formulation.

We claim:

1. A stabilized patch device for transdermal delivery of a steroid drug containing a 3-keto-4-en functional group, wherein said steroid drug is stable upon storage of said device, comprising an effective amount of said steroid drug and a biocompatible polymeric adhesive with which said steroid drug is intimately admixed, wherein said polymeric adhesive is a block copolymer of N-vinyl pyrrolidone and 2-ethyl-hexyl acrylate.

2. The stabilized patch device of claim 1 wherein said steroid drug is selected from the group consisting of sex hormones and corticosteroids that have said 3-keto-4-en functional group.

3. The stabilized patch device of claim 2 wherein said steroid drug is a sex hormone selected from the group consisting of progestins that have said 3-keto-4-en functional group, androgens that have said 3-keto-4-en functional group, and mixtures thereof.

4. The stabilized patch device of claim 3 wherein said sex hormone is a progestin that has said 3-keto-4-en functional group and said progestin is a member selected from the group consisting of progesterone, ethisterone (17α-ethinyltestosterone), medroxyprogesterone, hydroxyprogesterone, norethindrone (17α-ethinyl-19-nortestosterone), norethindrone acetate (17α-ethinyl-19-nortestosterone acetate), dydrogesterone (9β,10α-pregna-4,6-diene-3,20-dione), dimethisterone (6α-methyl-17α-|1-propynyl|-testosterone), chlormadinone acetate (6-chloro-6-dehydro-17α-acetoxyprogesterone), norgestrel (13β-ethyl-17α-ethinyl-17β-hydroxygon-4-en-3-one), and esters and mixtures thereof.

5. The stabilized patch device of claim 4 wherein said progestin is norethindrone acetate.

6. The stabilized patch device of claim 4 wherein said progestin is norethindrone.

7. The stabilized patch device of claim 4 wherein said progestin is levonorgestrel.

8. The stabilized patch device of claim 3 wherein said sex hormone is an androgen that has said 3-keto-4-en functional group and said androgen is a member selected from the group consisting of testosterone, methyltestosterone, fluoxymesterone, methandrostenolone, nandrolone, norethandrolone, and esters and mixtures thereof.

9. The stabilized patch device of claim 8 wherein said androgen is a member selected from the group consisting of testosterone and esters thereof.

10. The stabilized patch device of claim 2 wherein said steroid drug is a corticosteroid that has said 3-keto-4-en functional group and said corticosteroid is a member selected from the group consisting of hydroxycortisone, cortisone, desoxycorticosterone, fludrocortisone, betamethasone, dexamethasone, prednisolone, prednisone, methylprednisolone, paramethasone, triamcinolone, flumethasone, fluocinolone, fluocinonide, fluprednisolone, halcinonide, flurandrenolide, meprednisone, medrysone, and esters and mixtures thereof.

11. The stabilized patch device of claim 1 further comprising a penetration enhancer selected from the group consisting of envelope disordering compounds, solvents, and mixtures thereof.

12. The stabilized patch device of claim 11 wherein said cell envelope disordering compounds are selected from the group consisting of isopropyl myristate, methyl laurate, oleyl alcohol, glycerol monooleate, glycerol dioleate, glycerol trioleate, glycerol monostearate, glycerol monolaurate, propylene glycol monolaurate, and sorbitan esters and mixtures thereof, and said solvents are selected from the group consisting of water, diols, mono-alcohols, DMSO, dimethylformamide, N,N-dimethylacetamide, 2-pyrrolidone, azones, and mixtures thereof.

13. The stabilized patch device of claim 2 further comprising a steroid not containing a 3-keto-4-en functional group selected from the group consisting of estrogens, progestins not containing a 3-keto-4-en functional group, androgens not containing a 3-keto-4-en functional group, and corticosteroids not containing a 3-keto-4-en functional group.

14. The stabilized patch device of claim 13 wherein said steroid not containing a 3-keto-4-en functional group in an estrogen.

15. The stabilized patch device of claim 14 wherein said estrogen is an estradiol.

16. A method of stabilizing a steroid drug containing a 3-keto-4-en functional group during storage of a transdermal drug delivery patch device containing said steroid drug comprising the steps of (a) first intimately admixing an effective amount of said steroid drug with an effective amount of a block copolymer of N-vinyl pyrrolidone and 2-ethyl-hexyl acrylate, and (b) then incorporating said admixed steroid drug and block copolymer of N-vinyl pyrrolidone and 2-ethyl-hexyl acrylate into said delivery patch device as a source of said steroid drug.

17. The method of claim 16 wherein said steroid drug is selected from the group consisting of sex hormones and corticosteroids that have a 3-keto-4-en functional group.

18. The method of claim 17 wherein said steroid drug is a sex hormone selected from the group consisting of progestins that have a 3-keto-4-en functional group, androgens that have a 3-keto-4-en functional group, and mixtures thereof.

19. The method of claim 18 wherein said sex hormone is a progestin that has said 3-keto-4-en functional group and said progestin is a member selected from the group consisting of progesterone, ethisterone (17α-ethinyltestosterone), medroxyprogesterone, hydroxyprogesterone, norethindrone (17α-ethinyl-19-nortestosterone), norethindrone acetate (17α-ethinyl-19-nortestosterone acetate), dydrogesterone (9β,10α-pregna-4,6-diene-3,20-dione), dimethisterone (6α-methyl-17α-[1-propynyl]-testosterone), chlormadinone acetate (6-chloro-6-dehydro-17α-acetoxyprogesterone), norgestrel (13β-ethyl-17α-ethinyl-17β-hydroxygon-4-en-3-one), and esters and mixtures thereof.

20. The method of claim 19 wherein said progestin is norethindrone acetate.

21. The method of claim 19 wherein said progestin is norethindrone.

22. The method of claim 19 wherein said progestin is levonorgestrel.

23. The method of claim 18 wherein said sex hormone is an androgen that has said 3-keto-4-en functional group and said androgen is a member selected from the group consisting of testosterone, methyltestosterone, fluoxymesterone, methandrostenolone, nandrolone, norethandrolone, and esters and mixtures thereof.

24. The method of claim 23 wherein said androgen is a member selected from the group consisting of testosterone and esters thereof.

25. The method of claim 17 wherein said steroid drug is a corticosteroid that has said 3-keto-4-en functional group and said corticosteroid is a member selected from the group consisting of hydroxycortisone, cortisone, desoxycorticosterone, fludrocortisone, betamethasone, dexamethasone, prednisolone, prednisone, methylprednisolone, paramethasone, triamcinolone, flumethasone, fluocinolone, fluocinonide, fluprednisolone, halcinonide, flurandrenolide, meprednisone, medrysone, and esters and mixtures thereof.

26. The method of claim 16 further comprising a penetration enhancer selected from the group consisting of cell envelope disordering compounds, solvents, and mixtures thereof.

27. The method of claim 26 wherein said cell envelope disordering compounds are selected from the group consisting of isopropyl myristate, methyl laurate, oleyl alcohol, glycerol monooleate, glycerol dioleate, glycerol trioleate, glycerol monostearate, glycerol monolaurate, propylene glycol monolaurate, and sorbitan esters and mixtures thereof, and said solvents are selected from the group consisting of water, diols, mono- alcohols, DMSO, dimethylformamide, N,N-dimethylacetamide, 2-pyrrolidone, azones, and mixtures thereof.

28. The method of claim 17 further comprising a steroid not containing a 3-keto-4-en functional group selected from the group consisting of estrogens, progestins not containing a 3-keto-4-en functional group, androgens not containing a 3-keto-4-en functional group, and corticosteroids not containing a 3-keto-4-en functional group.

29. The method of claim 28 wherein said steroid not containing a 3-keto-4-en functional group in an estrogen.

30. The method of claim 29 wherein said estrogen is estradiol.

* * * * *